(12) United States Patent
Yoo et al.

(10) Patent No.: US 9,437,036 B2
(45) Date of Patent: Sep. 6, 2016

(54) MEDICAL SYSTEM, MEDICAL IMAGING APPARATUS, AND METHOD OF PROVIDING THREE-DIMENSIONAL MARKER

(71) Applicant: SAMSUNG MEDISON CO., LTD., Hongcheon-gun, Gangwon-do (KR)

(72) Inventors: Jun-sang Yoo, Gangwon-do (KR); Sung-yoon Kim, Gangwon-do (KR); Han-jun Kim, Gangwon-do (KR); Jun-Kyo Lee, Gangwon-do (KR)

(73) Assignee: SAMSUNG MEDISON CO., LTD., Gangwon-Do (KR)

( * ) Notice: Subject to any disclaimer, the term of this patent is extended or adjusted under 35 U.S.C. 154(b) by 75 days.

(21) Appl. No.: 14/096,887

(22) Filed: Dec. 4, 2013

(65) Prior Publication Data
US 2014/0152656 A1    Jun. 5, 2014

(30) Foreign Application Priority Data

Dec. 4, 2012 (KR) .................. 10-2012-0139468
Dec. 4, 2013 (KR) .................. 10-2013-0150038

(51) Int. Cl.
*G06T 15/00* (2011.01)
*G06T 15/08* (2011.01)
(Continued)

(52) U.S. Cl.
CPC .............. *G06T 15/08* (2013.01); *A61B 8/466* (2013.01); *A61B 8/469* (2013.01); *A61B 8/483* (2013.01);
(Continued)

(58) Field of Classification Search
CPC . G06T 15/08; G06T 2210/41; G06T 7/0081; G06T 2207/10136; G06T 2207/20101; G01S 7/52073; G01S 15/8993; A61B 8/466; A61B 8/469; A61B 8/483

USPC ........ 345/419, 420, 422; 382/100; 600/407, 600/443, 637
See application file for complete search history.

(56) References Cited

U.S. PATENT DOCUMENTS 5,934,288 A * 8/1999 Avila et al. .................. 600/443
6,241,675 B1 * 6/2001 Smith et al. ................. 600/443
(Continued)

FOREIGN PATENT DOCUMENTS

EP     2208467 A1    7/2010
EP     2524652 A1    11/2012
(Continued)

OTHER PUBLICATIONS

Kutter et al, Visulization and GPU-accelerated Simulation of Medical Ultrasound from CT images, Computer Methods and Programs in Biomedicine 94, 2009, pp. 250-266.*
(Continued)

*Primary Examiner* — Phu K Nguyen
(74) *Attorney, Agent, or Firm* — McDermott Will & Emery LLP

(57) ABSTRACT

A medical system, a medical imaging apparatus, and a method of setting a 3-dimensional (3D) marker on a 3D image are provided. The medical imaging apparatus a display unit displaying a 3-dimensional (3D) ultrasound image generated by using 3D data; a user input unit receiving first input information for selecting a predetermined point of the 3D ultrasound image; and a processor detecting 3D geometry information of a 3D marker that corresponds to the predetermined point in the 3D data based on the first input information, and setting the 3D marker on the 3D image based on the 3D geometry information that is detected.

16 Claims, 9 Drawing Sheets

(51) Int. Cl.
*A61B 8/00* (2006.01)
*G01S 15/89* (2006.01)
*G06T 7/00* (2006.01)
*G01S 7/52* (2006.01)
*A61B 8/08* (2006.01)

(52) U.S. Cl.
CPC ........ *G01S 7/52063* (2013.01); *G01S 7/52073* (2013.01); *G01S 15/8993* (2013.01); *G06T 7/0081* (2013.01); *G06T 2207/10136* (2013.01); *G06T 2207/20101* (2013.01); *G06T 2207/20141* (2013.01); *G06T 2210/41* (2013.01)

(56) References Cited

U.S. PATENT DOCUMENTS

| | | | | |
|---|---|---|---|---|
| 7,493,153 | B2* | 2/2009 | Ahmed | A61B 19/52 345/7 |
| 8,591,420 | B2* | 11/2013 | Hamada | 600/443 |
| 8,768,022 | B2* | 7/2014 | Miga | A61B 19/52 345/420 |
| 9,248,316 | B2* | 2/2016 | Lachaine | A61N 5/1049 |
| 2005/0240104 | A1* | 10/2005 | Shim et al. | 600/437 |
| 2006/0058605 | A1* | 3/2006 | Deischinger et al. | 600/407 |
| 2008/0044054 | A1* | 2/2008 | Kim et al. | 382/100 |
| 2010/0030079 | A1 | 2/2010 | Hamada | |
| 2012/0245465 | A1 | 9/2012 | Hansegard et al. | |
| 2014/0005545 | A1 | 1/2014 | Lee et al. | |

FOREIGN PATENT DOCUMENTS

| | | |
|---|---|---|
| JP | 2006-212164 A | 8/2006 |
| KR | 10-2014-0000299 A | 1/2014 |

OTHER PUBLICATIONS

Unlu et al, Computerized Method for Nonrigid MR-to-PET breast-image registration, Computers in Biology and medicine 40, 2010, pp. 37-53.*

Wolf I et al., "Visualization techniques for improved orientation in three-dimensional echocardiography", Proceedings of SPIE: Medical Imaging 2002: Visualization, Image-Guided Proceduires, and Display, SPIE-International Society for Optical Engineering, US; San Diego, CA, USA, vol. 4681, Jan. 2, 2002, pp. 380-387. XP008138746, ISSN: 0277-786X, DOI: 10.1117/12.466941.

European Extended Search Report issued in European Patent Application No. 13195760.7 dated Mar. 4, 2014.

Korean Intellectual Property Office (KIPO). 2016. Notice of Allowance, dated Jan. 20, 2016, for counterpart Korean application 10-2015-181101.

* cited by examiner

MEDICAL SYSTEM, MEDICAL IMAGING APPARATUS, AND METHOD OF PROVIDING THREE-DIMENSIONAL MARKER

RELATED APPLICATIONS

This application claims the benefit of Korean Patent Application No. 10-2012-0139468 filed on Dec. 4, 2012, and Korean Patent Application No. 10-2013-0150038 filed on Dec. 4, 2013 in the Korean Intellectual Property Office, the disclosure of which is incorporated herein in its entirety by reference.

BACKGROUND

1. Field

One or more embodiments of the present invention relate to a medical system, and more particularly, to a medical system, a medical imaging apparatus, and a method of providing a 3-dimensional (3D) marker.

2. Description of the Related Art

A medical system provides an image of an object, and is used in various fields. The medical system includes a magnetic resonance image (MRI) system, a computed tomography (CT) system, a positron emission tomography (PET-CT) system, an ultrasonic system, and the like. Hereinafter, for the convenience of description, the medical system is referred to as an ultrasonic system that provides an ultrasonic image of an object.

The ultrasonic system is non-invasive and non-destructive, and thus is widely used in the medical field so as to obtain information regarding the inside of the object. The ultrasonic system provides high-resolution images of the inside of the object to medical doctors in real-time, without the need of an intrusive surgical operation that requires directly cutting into the object in order to obtain information regarding the inside thereof. Thus, the ultrasonic system is an important device in the medical field.

The ultrasonic system provides 3-dimensional (3D) ultrasound images that include clinical information such as spatial information and anatomical information, which may not be provided in 2-dimensional (2D) ultrasound images. In the ultrasound system, the 3D ultrasound images are generated by sequentially transmitting ultrasonic signals to the object, receiving ultrasonic signals that are reflected from the object (i.e., ultrasonic echo signals), generating 3D data (i.e., volume data), and then, volume rendering the 3D data.

At least one marker for showing a region of interest in an ultrasound image may be set in the ultrasonic system. In the related art, a 2D marker may be set on the 2D ultrasound images. Alternatively, in order to set a marker on the 3D ultrasound images, the 2D marker may be set on sectional images (i.e., the 2D ultrasound images) that correspond to the 3D ultrasound images. Therefore, there is a need for a system for directly setting a 3D marker on the 3D ultrasound images.

SUMMARY

One or more embodiments of the present invention include a medical system and a method of detecting 3-dimensional (3D) geometry information of a 3D marker based on 3D data, and setting the 3D marker on a 3D image that corresponds to the 3D data by using the detected 3D geometry information.

Additional aspects will be set forth in part in the description which follows and, in part, will be apparent from the description, or may be learned by practice of the presented embodiments.

According to one or more embodiments of the present invention, a medical system includes an image data obtaining unit obtaining image data that corresponds to a 3-dimensional (3D) image of an object, the object comprising a target object; a user input unit receiving input information; and a processor generating 3D data by using the image data, generating the 3D image by using the 3D data, detecting 3D geometry information that corresponds to a 3D marker in the 3D data based on the input information, and setting the 3D marker on the 3D image based on the 3D geometry information that is detected.

According to one or more embodiments of the present invention, a method of setting a 3D marker, the method includes a) obtaining image data that corresponds to a 3-dimensional (3D) image of an object, the object comprising a target object; b) generating 3D data by using the image data; c) generating the 3D image by using the 3D data; d) receiving input information of the user; e) detecting 3D geometry information that corresponds to the 3D marker in the 3D data based on the input information; and f) setting the 3D marker on the 3D image based on the 3D geometry information that is detected.

According to one or more embodiments of the present invention, a medical imaging apparatus includes a display unit displaying a 3-dimensional (3D) ultrasound image generated by using 3D data, a user input unit receiving first input information for selecting a predetermined point of the 3D ultrasound image, and a processor detecting 3D geometry information of a 3D marker that corresponds to the predetermined point in the 3D data based on the first input information, and setting the 3D marker on the 3D image based on the 3D geometry information that is detected.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
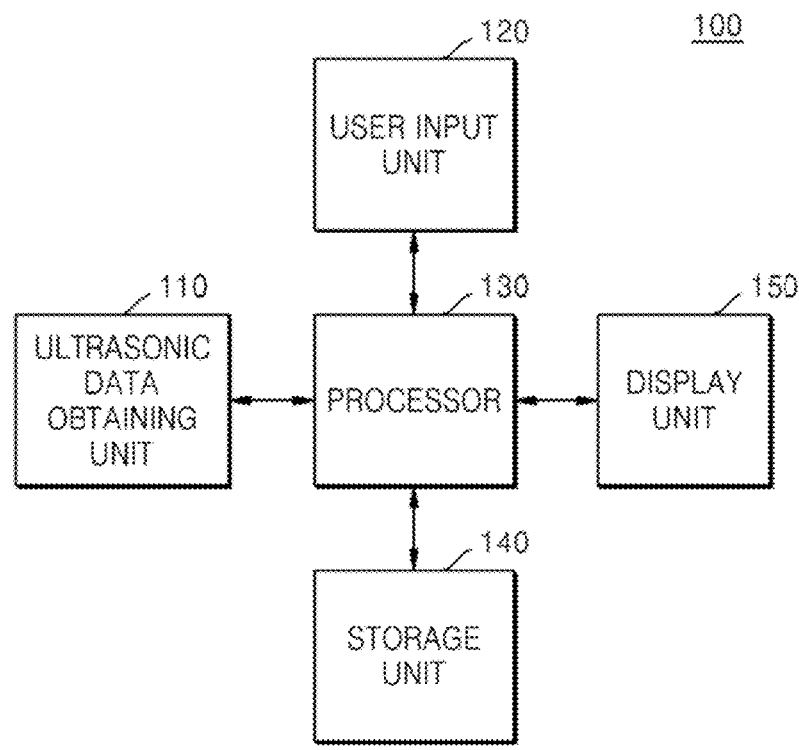
FIG. 1 is a block diagram illustrating an ultrasonic system according to an embodiment of the present invention.

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, expressions such as "at least one of," when preceding a list of elements, modify the entire list of elements and do not modify the individual elements of the list.

For the convenience of description, a medical system is referred to as an ultrasonic system. However, the medical system is not limited thereto, and includes a magnetic resonance image (MRI) system, a computed tomography (CT) system, a positron emission tomography (PET-CT) system, and the like.

FIG. 1 is a block diagram illustrating an ultrasonic system 100 according to an embodiment of the present invention. Referring to FIG. 1, the ultrasonic system 100 includes an ultrasonic data obtaining unit 110, a user input unit 120, a processor 130, a storage unit 140, and a display unit 150.

The ultrasonic data obtaining unit 110 obtains ultrasonic data that corresponds to an ultrasound image of an object. The object includes a target object (e.g., blood vessels, heart, liver, and bones). The ultrasonic data includes radio frequency (RF) data, but is not limited thereto.

Figure 2:
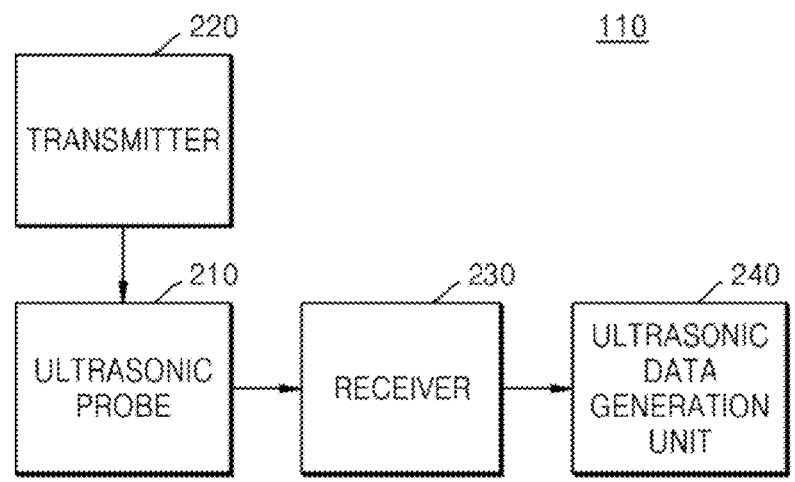
FIG. 2 is a block diagram illustrating an ultrasonic data obtaining unit, according to an embodiment of the present invention.

FIG. 2 is a block diagram illustrating the ultrasonic data obtaining unit 110, according to an embodiment of the present invention. Referring to FIG. 2, the ultrasonic data obtaining unit 110 includes an ultrasonic probe 210, a transmitter 220, a receiver 230, and an ultrasonic data generation unit 240.

The ultrasonic probe 210 includes a plurality of transducer elements (not shown) that mutually converts electric signals and ultrasonic signals. The ultrasonic probe 210 transmits ultrasonic signals to the object, receives ultrasonic echo signals that are reflected from the object (i.e., ultrasonic echo signals that are reflected from the object in response to the ultrasonic signals transmitted to the object), and thus generates electric signals (hereinafter, referred to as "reception signals"). The reception signals are analog signals. The ultrasonic probe 210 includes a 3-dimensional (3D) probe, a 2-dimensional (2D) array probe, and the like.

Figure 3:
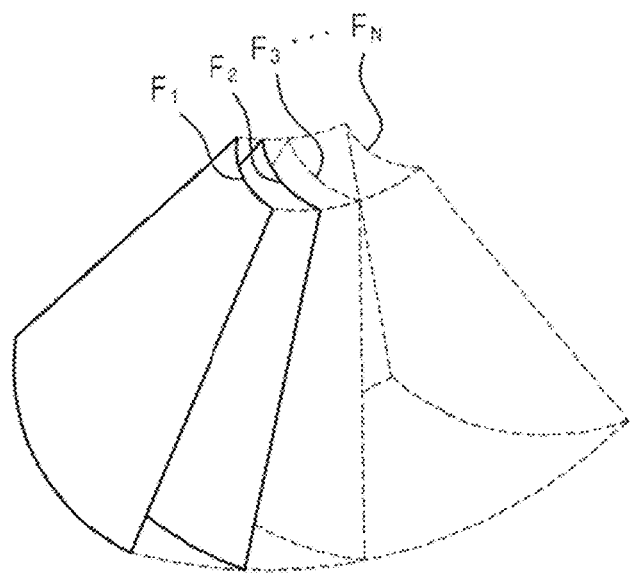
FIG. 3 is an exemplary view of a plurality of frames.

The transmitter 220 controls transmission of the ultrasonic signals. Also, the transmitter 220 generates electric signals (hereinafter, referred to as "transmission signals") for obtaining the ultrasound image, regarding the transducer elements. According to the present embodiment, as illustrated in FIG. 3, the transmitter 220 generates the transmission signals for obtaining each of a plurality of frames ($F_i(1 \leq i \leq N)$), regarding the transducer elements. Therefore, the ultrasonic probe 210 converts the transmission signals that are sequentially provided by the transmitter 220 into the ultrasonic signals, transmits the ultrasonic signals to the object, receives the ultrasonic echo signals that are reflected from the object, and thus generates the reception signals.

The receiver 230 generates digital signals by analog-digital converting the reception signals provided by the ultrasonic probe 210. Also, regarding locations of the transducer elements, the receiver 230 performs reception beam forming, and thus generates focused reception signals. Since methods known to one of ordinary skill in the art may be used to perform reception beams forming, the methods will not be described in the present embodiment.

The ultrasonic data generation unit 240 generates the ultrasonic data that corresponds to the ultrasound image, by using the focused reception signals provided by the receiver 230. According to the present embodiment, the ultrasonic data generation unit 240 generates the ultrasonic data that respectively corresponds to the plurality of frames ($F_i$ ($1 \leq i \leq N$)), by using the focused reception signals that are sequentially provided by the receiver 230. Also, the ultrasonic data generation unit 240 may perform various types of signal processing (e.g., gain control) as necessary on the reception access signals to generate the ultrasonic data.

According to the embodiment described above, the ultrasonic data obtaining unit 110 obtains the ultrasonic data corresponding to the ultrasound image by transmitting the ultrasonic signals to the object, and receiving the ultrasonic echo signals that are reflected from the object. In other embodiments, the ultrasonic data obtaining unit 110 may obtain the ultrasonic data from an external or internal device (not shown) that is wired or connected wirelessly to the ultrasonic system 100.

Referring to FIG. 1, the user input unit 120 receives input information input. That is, the input information may input by a user. According to the present embodiment, the input information includes first input information for setting a point on a 3D ultrasound image, the point corresponding to a 3D marker. That is, the first input information includes a 2D coordinate value of a point which is set on the 3D ultrasound image and displayed on the display unit 150. Also, the input information includes second input information for selecting at least one target object from among a plurality of target objects in the object. In addition, the input information includes third input information which is used for setting a reference value for determining a location of the 3D marker in the 3D ultrasound image in a depth direction. However, the input information is not limited thereto. The user input unit 120 includes a control panel, a track ball, a touch screen, a keyboard, a mouse, and the like.

The processor 130 is connected to the ultrasonic data obtaining unit 110 and the user input unit 120. The processor 130 includes a central processing unit (CPU), a microprocessor, a graphic processing unit (GPU), and the like.

In the medical system according to an embodiment of the present invention, the display unit 150 displays the 3D ultrasound image that is generated by using 3D data.

The user input 120 receives the first input information for selecting a predetermined point of the 3D ultrasound image. Based on the first input information the processor 130 detects 3D geometry information of the 3D marker that corresponds to a predetermined point in the 3D data, and sets the 3D marker on the 3D image based on the 3D geometry information that is detected.

Figure 4:
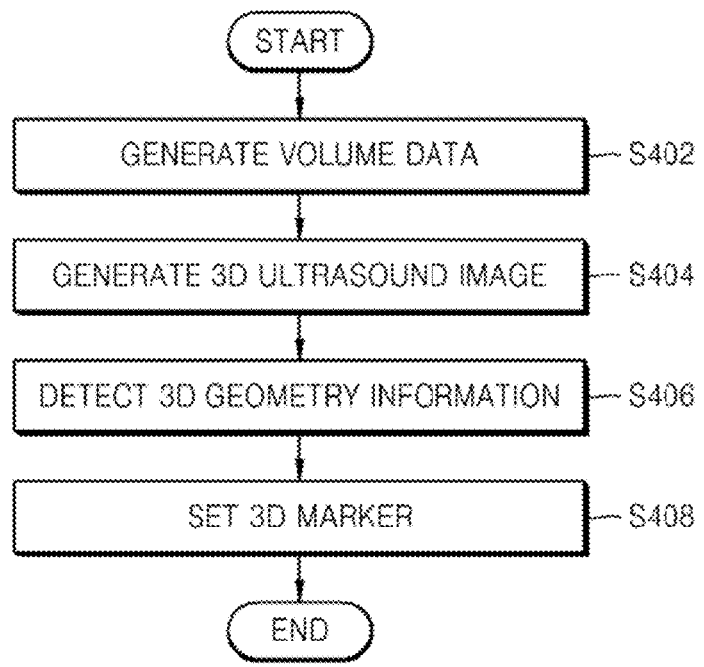
FIG. 4 is a flowchart illustrating a process of setting a 3-dimensional (3D) marker, according to an embodiment of the present invention.
Figure 5:
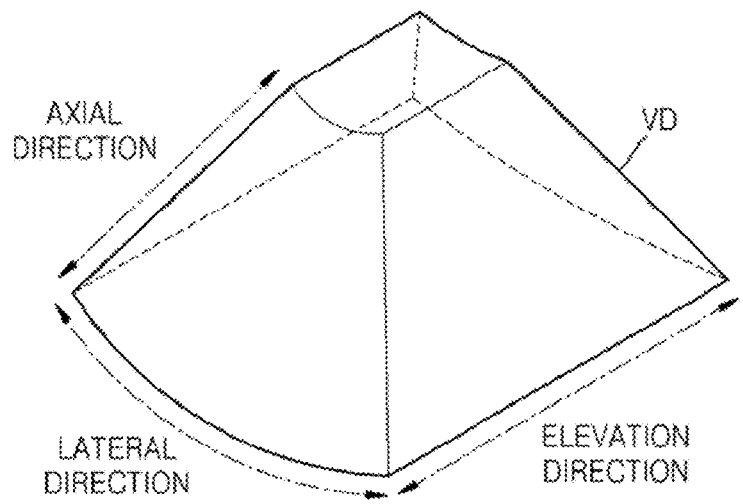
FIG. 5 is an exemplary view of volume data.

FIG. 4 is a flowchart illustrating a process of setting the 3D marker, according to an embodiment of the present invention. Referring to FIG. 4, the processor 130 uses the ultrasonic data that is provided by the ultrasonic data obtaining unit 110, and thus generates 3D data, that is, volume data VD, as illustrated in FIG. 5.

The volume data VD includes the plurality of frames ($F_i(1 \leq i \leq N)$), and a plurality of voxels having brightness values. Each of the plurality of voxels includes 3D geometry information (i.e., 3D coordinate values) regarding the volume data VD. In FIG. 5, an axial direction refers to a proceeding direction of the ultrasound signals, which is based on the transducer elements of the ultrasonic probe 210; a lateral direction refers to a moving direction of a scanline; and an elevation direction, which is the depth direction of the 3D ultrasound image, refers to a scanning direction of a frame (i.e., a scanning direction of a scanning area).

The processor 130 volume-renders volume data VD, and thus generates the 3D ultrasound image (S404). The volume-rendering method includes ray-casting, perspective rendering, and stereo-type rendering, but is not limited thereto. The 3D ultrasound image may be displayed on the display unit 150. Therefore, the user may set a point on the 3D ultrasound image that is displayed on the display unit 150, by using the user input unit 120.

Figure 6:
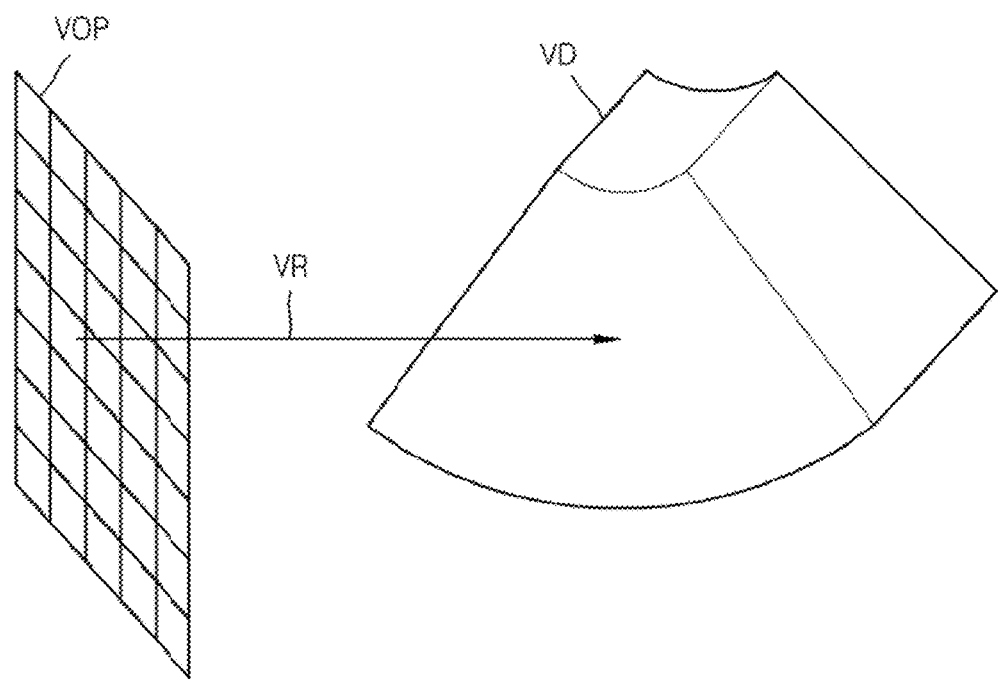
FIG. 6 is an exemplary view of volume-rendering.
Figure 7:
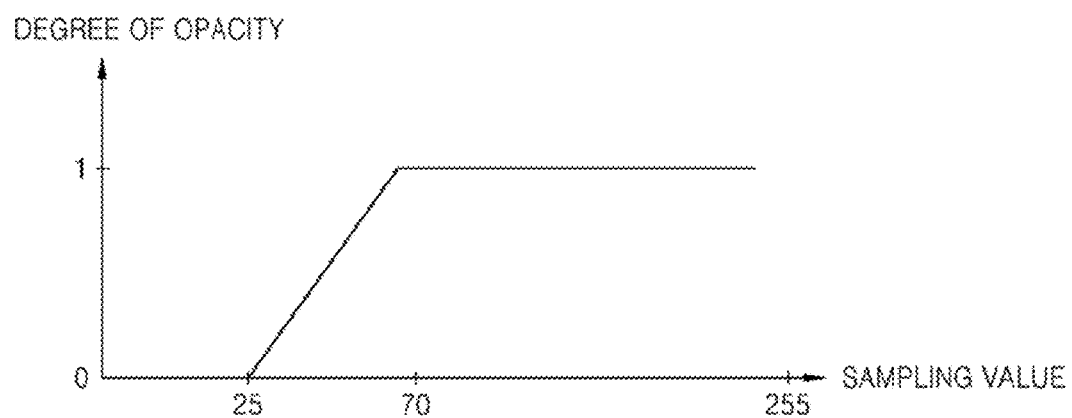
FIG. 7 is an exemplary view of an opacity transfer function.

For example, as illustrated in FIG. 6, the processor 130 sets a virtual observation plane VOP that is formed of a plurality of pixels, based on the volume data VD. The virtual observation plane VOP is a plane corresponding to a screen of the display unit 150, on which the 3D ultrasound image is displayed. The processor 130 projects a virtual ray VR from each of the plurality of pixels of the virtual observation plane VOP toward the volume data VD. The processor 130 obtains a sampling point and a sampling value of the sampling point by sampling the virtual ray with predetermined sampling intervals. For example, the processor 130 samplings the volume data VD of a track of the virtual ray at a predetermined sampling interval, and obtains the sampling point and a sampling value of the sampling point. A range of the sampling value may be 0 to about 255, but is not limited thereto. The processor 130 estimates a degree of opacity of a current sampling point by using an opacity transfer function. The opacity transfer function is a function that determines the degree of opacity according to the sampling value. As illustrated in FIG. 7, when the range of the sampling value is 0 to about 25, the degree of opacity is determined to be 0; when the range of the sampling value is about 25 to about 70, the degree of opacity is linearly determined to be a value between 0 and about 1; and when the range of the sampling value is about 70 to about 255, the degree of opacity is determined to be about 1. According to the sampling value and the degree of opacity, the processor 130 estimates pixel values that respectively correspond to the plurality of pixels of the virtual observation plane VOP.

According to the input information provided by the user input unit 120, the processor 130 detects the 3D geometry information (i.e., the 3D coordinate values) of a point in the volume data VD (i.e., the 3D ultrasound image) (S406). For example, the processor 130 detects the 3D coordinate value which is corresponding to a point input by the user in the 3D ultrasound image.

Figure 8:
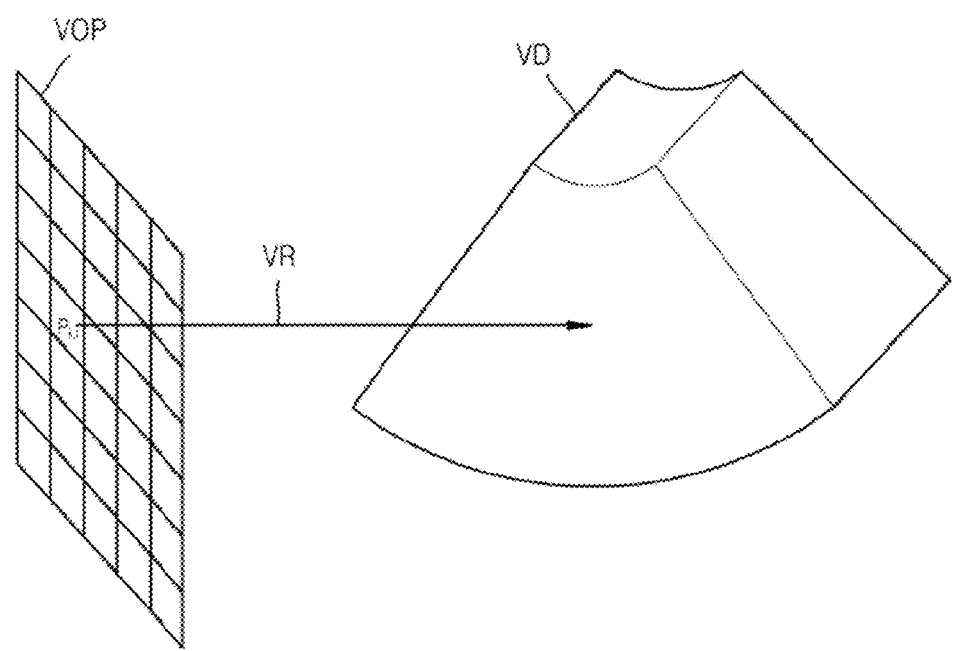
FIG. 8 is an exemplary view of an observation plane, a point, and a virtual ray, according to an embodiment of the present invention.

According to an embodiment of the present invention, based on the input information (i.e., second input information) provided by the user input unit 120, the processor 130 determines a reference value that corresponds to the target object. The predetermined reference value may be stored in the storage unit 140. For example, the processor 130 extracts the reference value matched to the second input information for selecting the target object, and determines the extracted reference value as the reference value corresponds to the target object. As illustrated in FIG. 6, the processor 130 sets the virtual observation plane VOP that is formed of a plurality of pixels based on the volume data VD. Based on the input information (i.e., first input information) provided by the user input unit 120, the processor 130 detects a pixel that corresponds to the point on the virtual observation plane VOP. That is, as illustrated in FIG. 8, the processor 130 detects a pixel $P_{i,j}$ that corresponds to the point, according to 2D location information (i.e., 2D coordinate values) of the point. As illustrated in FIG. 8, the processor 130 projects the virtual ray VR from the pixel $P_{i,j}$ that is detected to the volume data VD. The processor 130 obtains a sampling point and a sampling value of the sampling point by sampling on the virtual ray VR at a predetermined sampling interval. Based on the sampling value, the processor 130 detects a voxel that corresponds to a reference value from the volume data VD. For example, the processor 130 cumulatively adds a plurality of sampling values in a proceeding direction of the virtual ray VR, and then determines that a voxel, which has a sum of cumulatively added sampling values that is the first to exceed or be equal to the reference value, is the voxel that corresponds to the reference value. As another example, the processor 130 compares the plurality of sampling values and a predetermined threshold value, detects whether any of the plurality of sampling values are greater than or equal to the predetermined threshold value, cumulatively adds a plurality of sampling values that are detected in a proceeding direction of the virtual ray VR, and thus, determines that a voxel, which has a sum of cumulatively added sampling values that is the first to exceed or be equal to the reference value, is the voxel that corresponds to the reference value. As another example, the processor 130 compares the plurality of sampling values and the reference value, detects a sampling value that is the first to exceed or be equal to the reference value, and thus, determines that a voxel that corresponds to the detected sampling value is the voxel that corresponds to the reference value. The processor 130 determines that the detected 3D geometry information (i.e., the 3D coordinate values) of the voxel is the 3D geometry information (i.e., the 3D coordinate values) of the point (i.e., the 3D marker).

Figure 10:
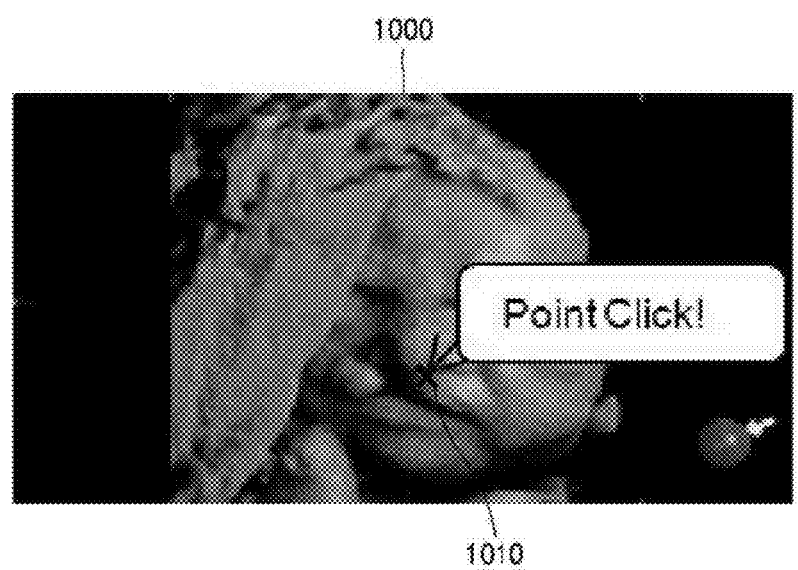
FIG. 10 is an exemplary view of a 3D ultrasound image.

In specific, referring to FIG. 10, the user may select a predetermined point 1010 on the 3D ultrasound image that is displayed on the display unit 150. Then, corresponding to the user's selection, the user input unit 120 receives first input information that is related to the predetermined point 1010 that is selected. Here, the predetermined point 1010 corresponds to a marker displayed on the 3D ultrasound image.

Figure 11:
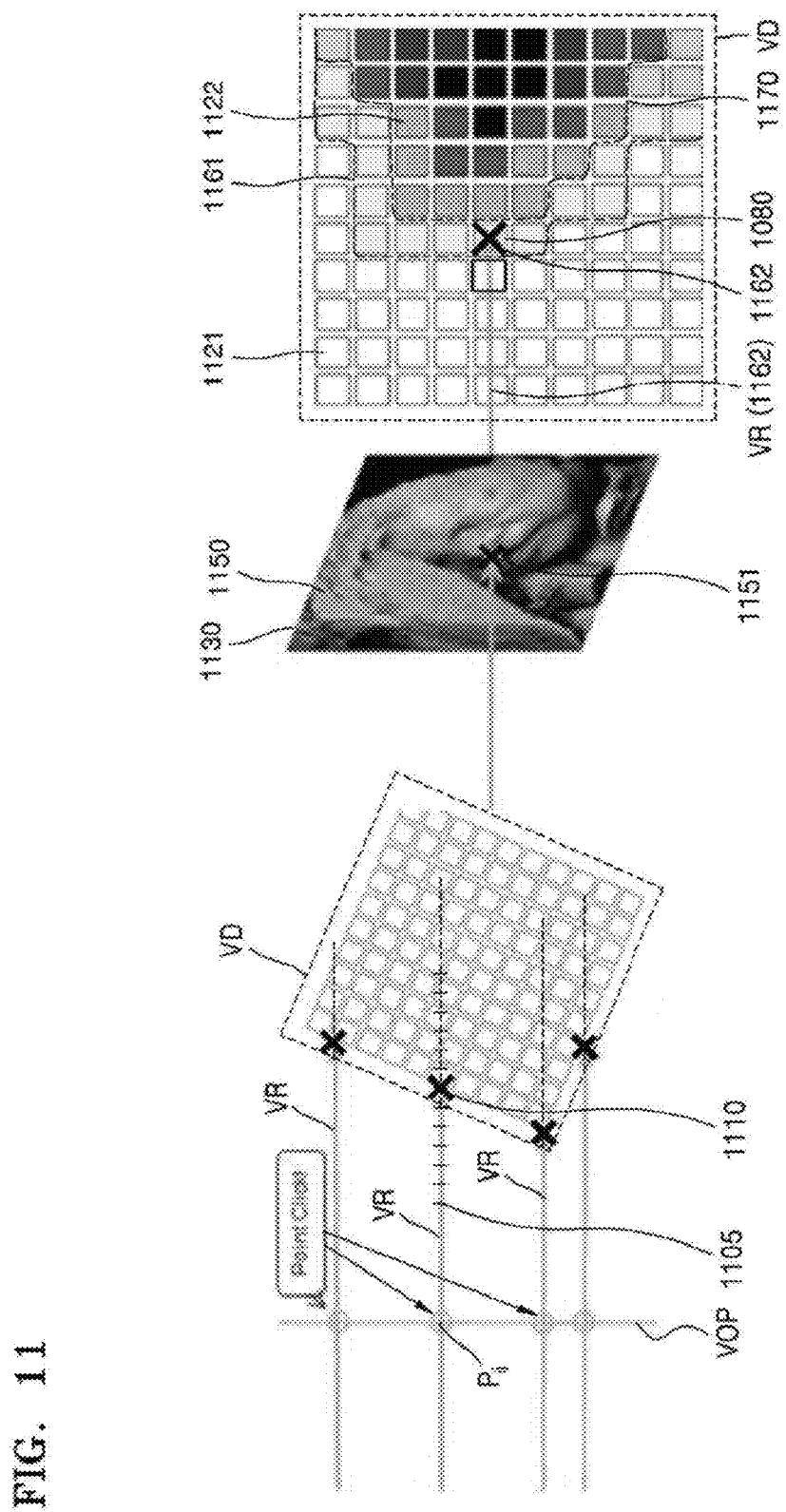
FIG. 11 is another exemplary view of an observation plane, a point, and a plurality of virtual rays, according to an embodiment of the present invention.

FIG. 11 illustrates an object 1150 that is included in a 3D ultrasound image 1130 displayed on the display unit 150. The user may select a predetermined point 1151 of the object 1150 by using the user input unit 120. Also, the user may select a plurality of points.

Referring to FIG. 11, volume data VD that corresponds to the 3D ultrasound image 1130 includes a plurality of voxels 1121 and 1122. The plurality of voxels 1121 and 1122 may be shown by using brightness values that correspond to brightness values of ultrasound images. For example, in FIG. 11, voxels at a portion 1170 where the object 1150 is located may be darkly displayed; voxels (such as voxels 1122) at a portion where the object 1150 is not located may be brightly displayed.

Referring to FIG. 11, a pixel $P_{i,j}$ that corresponds to the predetermined point 1151 selected on a virtual observation plane VOP is detected. As illustrated in FIG. 10, the processor 130 projects the virtual ray VR from the pixel $P_{i,j}$ that is detected to the volume data VD. The processor 130 obtains a sampling point 1105 and a sampling value of the sampling point 1105 by sampling on the virtual ray VR at a predetermined sampling interval. Based on the sampling value, the processor 130 detects a voxel that corresponds to a reference value from the volume data VD.

In specific, during the cumulatively adding of a plurality of sampling values in a proceeding direction of the virtual ray VR in the volume data VR, the sampling values change before and after a boundary 1161 of the object 1150. Here, the sampling values may correspond to the brightness values of the voxels. When a reference value is set as a sum of cumulatively added sampling values from the pixel $P_{i,j}$ to a sampling point 1162 on the boundary 1161 of the object 1150, a voxel, which has a sum of cumulatively added sampling values that is the first to exceed or be equal to the reference value, may be a voxel 1180 that is in the boundary 1161. Therefore, the processor 130 may detect the voxels 1180. Also, the processor 130 may obtain 3D coordinate values of the voxel 1180 as the 3D coordinate values of the 3D marker.

According to another embodiment of the present invention, the processor 130 determines a reference value that corresponds to the target object, based on the input information (i.e., the second input information and the third input information) provided by the user input unit 120. As described above, the processor 130 detects the 3D geometry information (i.e., the 3D coordinate values) of the point, according to the determined reference value.

The processor 130 sets the 3D marker on the 3D ultrasound image, based on the 3D geometry information (i.e., the 3D coordinate values) of the point (S408).

Alternatively, the processor 130 may seta random section in volume data VD, thus generating a sectional image corresponding to the random section that is set by using the volume data VD, and then set a 2D marker on the sectional image, based on the 3D geometry information of the 3D marker.

Figure 9:
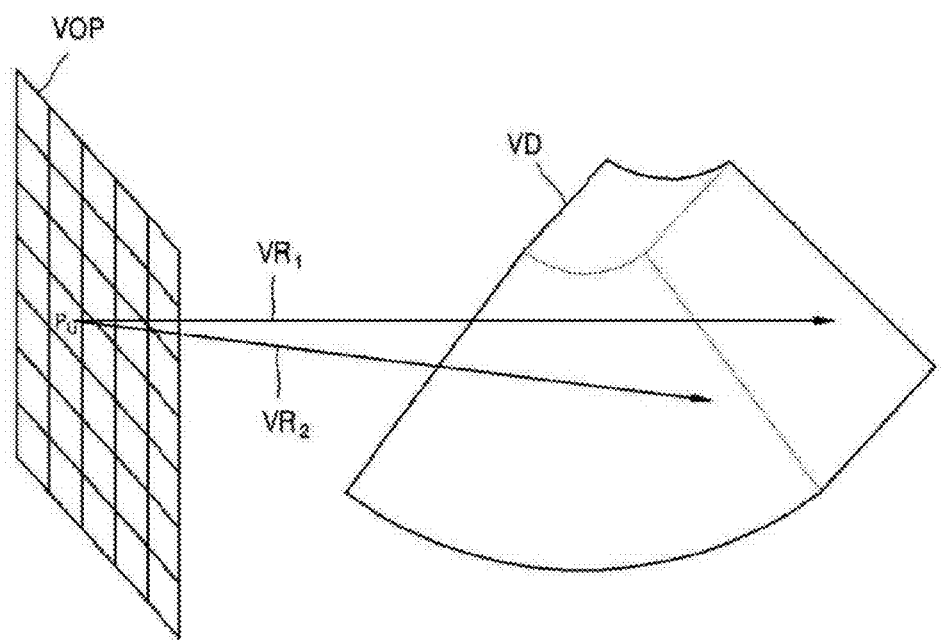
FIG. 9 is another exemplary view of an observation plane, a point, and a plurality of virtual rays, according to an embodiment of the present invention.

Alternatively, the processor 130 may show a depth of the 3D marker by using a stereo method for generating stereoscopic effect of the 2D marker. That is, as illustrated in FIG. 9, the processor 130 may project at least two virtual rays (e.g., VR1 and VR2) that respectively correspond to different angles, from the pixel $P_{i,j}$ that corresponds to the point in the volume data VD. Accordingly, the 3D marker may be set on an empty space which may not be displayed by using the ray-casting method. Also, the 3D marker may be set on an inner portion of the target object, which is difficult to set the 3D marker by using the ray-casting method.

Alternatively, the processor 130 may use a perspective ray-casting method to display the 3D marker on the 3D ultrasound image.

Figure 12:
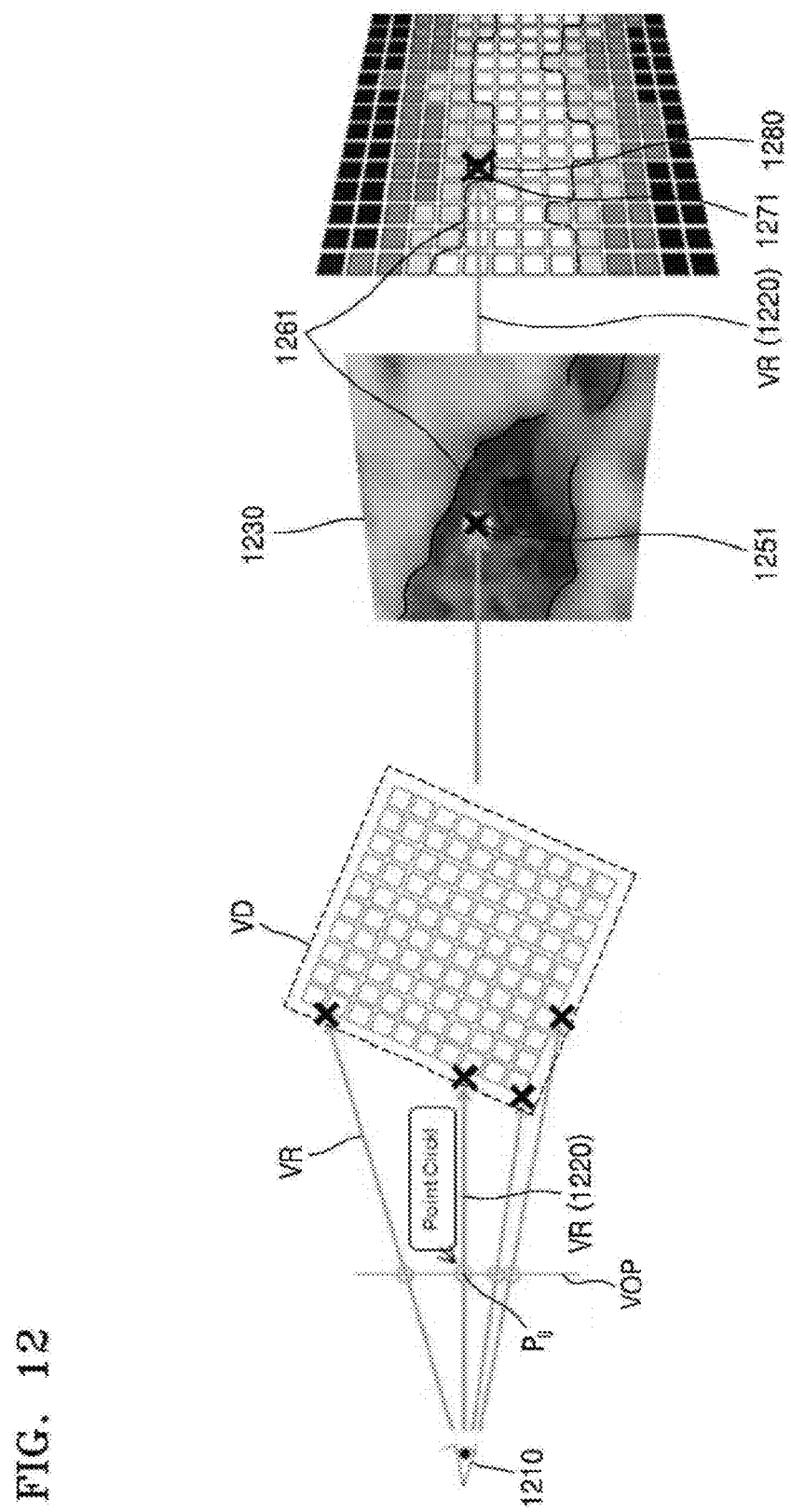
FIG. 12 is an exemplary view of ray-casting that is used in an ultrasound system according to an embodiment of the present invention.

FIG. 12 illustrates a case where a perspective-rendered 3D image 1230 having stereoscopic effect is displayed on the display unit 150, and a predetermined point 1251 is selected from the perspective-rendered 3D image 1230. Also, FIG. 12 illustrates the perspective-rendered 3D image 1230 corresponds to blood vessels, and volume data VD that corresponds to the perspective-rendered 3D image 1230. In the volume data VD, due to the perspective-rendered 3D image 1230, a size of an object seems smaller when the object is in a direction further away from a user's viewpoint 1210.

When the predetermined point 1261 is input in the perspective-rendered 3D image 1230, the processor 130 detects a pixel $P_{i,j}$ that corresponds to a point on a virtual observation plane VOP, based on first input information that includes information regarding the predetermined point 1251. As illustrated in FIG. 12, the processor 130 projects a virtual ray VR 1220 in a direction from the user's viewpoint 1210 which corresponds to the perspective-rendered 3D image 1230 to the pixel $P_{i,j}$. The processor 130 obtains a sampling point and a sampling value of the sampling point by sampling on the virtual ray VR at a predetermined sampling interval. Then, based on the sampling value, the processor 130 may detect a voxel that corresponds to a reference value from the volume data VD.

In specific, as in FIG. 11, when the reference value is set as a sum of cumulatively added sampling values from the pixel $P_{i,j}$ to a sampling point 1271 on a boundary 1261 of the object, a voxel, which has a sum of cumulatively added sampling values that is the first to exceed or be equal to the reference value, may be a voxel 1280 that is in the boundary 1261. Also, the processor 130 may obtain 3D coordinate values of the voxel 1280 as the 3D coordinate values of the 3D marker.

Also, in FIG. 12, the user's viewpoint 1210 may be obtained by using the perspective-rendered 3D image 1230. For example, depth information may be included in the perspective-rendered 3D image 1230. Therefore, location information of the user's viewpoint 1210 regarding the perspective-rendered 3D image 1230 may be obtained by using the depth information. Thus, the processor 130 may obtain the location information of the user's viewpoint 1210 by using the depth information of the perspective-rendered 3D image 1230.

Figure 13:
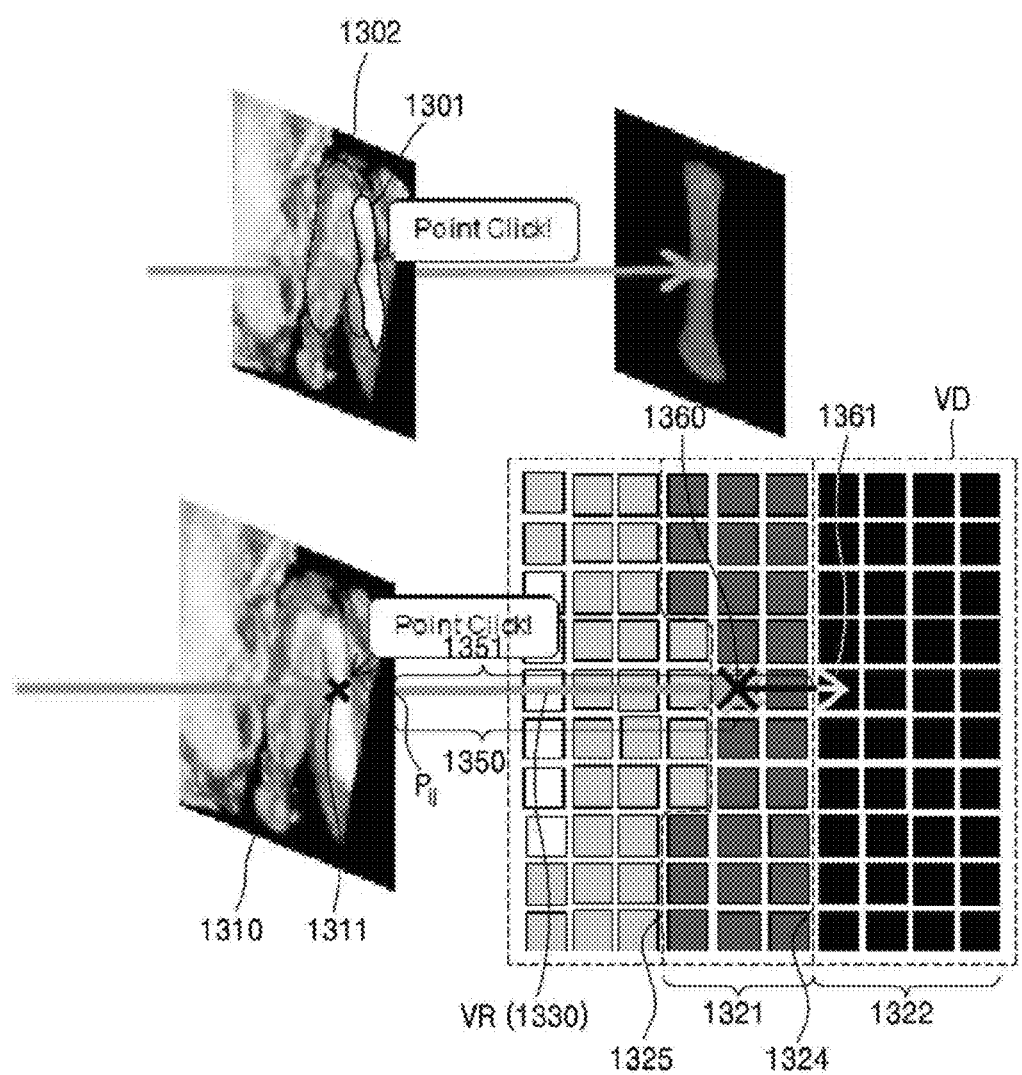
FIG. 13 is another exemplary view of an observation plane, a point, and a plurality of virtual rays, according to an embodiment of the present invention.

FIG. 13 illustrates a 3D ultrasound image 1310 showing a leg of a fetus. The brightness of pixes in the 3D ultrasound image 1310 changes as body parts change. In specific, as illustrated in FIG. 13, a bone 1301 is brightly displayed, and a tissue 1302 near the bone 1301 is darkly displayed than the bone 1301. Therefore, a bone portion 1322 may darkly displayed, and a tissue portion 1321 near the bone portion 1322 may be brightly displayed than the bone portion 1322.

When the user selects a predetermined point 1311 on the leg of the fetus in the 3D ultrasound image 1310, the processor 130 projects a virtual VR 1330, as in FIG. 11. The processor 130 obtains a sampling point and a sampling value of the sampling point by sampling on the virtual ray VR 1330 at a predetermined sampling interval. Based on the sampling value, the processor 130 detects a voxel that corresponds to a reference value from volume data VD.

In this case, the reference value may be vary according to a location of an object to be marked.

For example, when a point on a boundary 1324 of the bone 1301 is to be marked, the reference value may be sat as a sum of cumulatively added sampling values on a virtual ray VR 1351 that extends from a pixel $P_{i,j}$ to a sampling point on the boundary 1324 of the bone 1301. In this case, a voxel, which has a sum of cumulatively added sampling values that is the first to exceed or be equal to the reference value, may be a voxel 1361 in the boundary 1324 of the bone 1301. The processor 130 may detect the voxel 1361, and obtain 3D coordinate values of the voxel 1361 as the 3D coordinate values of the 3D marker. As another example, when the tissue 1302 near the bone 1301 is to be marked, the reference value may be set as a sum of cumulatively added sampling values on a virtual ray VR 1360 that extends from the pixel $P_{i,j}$ to a boundary 1325 of the tissue portion 1324. In this case, a voxel, which has a sum of cumulatively added sampling values that is the first to exceed or be equal to the reference value, may be a voxel 1360 in the boundary 1325 of the tissue portion 1321. The processor 130 may detect the voxel 1360, and obtain 3D coordinate values of the voxel 1360 as the 3D coordinate values of the 3D marker.

As described above, the processor 130 may adjust the reference value, and thus obtain 3D coordinate values of a marker at any location that is passed by the virtual ray VR.

Accordingly, the processor 130 may 3-dimensionally display the marker in a 3D image by using the 3D coordinate values of the marker.

Also, as described above, when the 3D coordinate values of the marker are obtained, the processor 130 may show a depth of the marker by using the stereo method.

Figure 14:
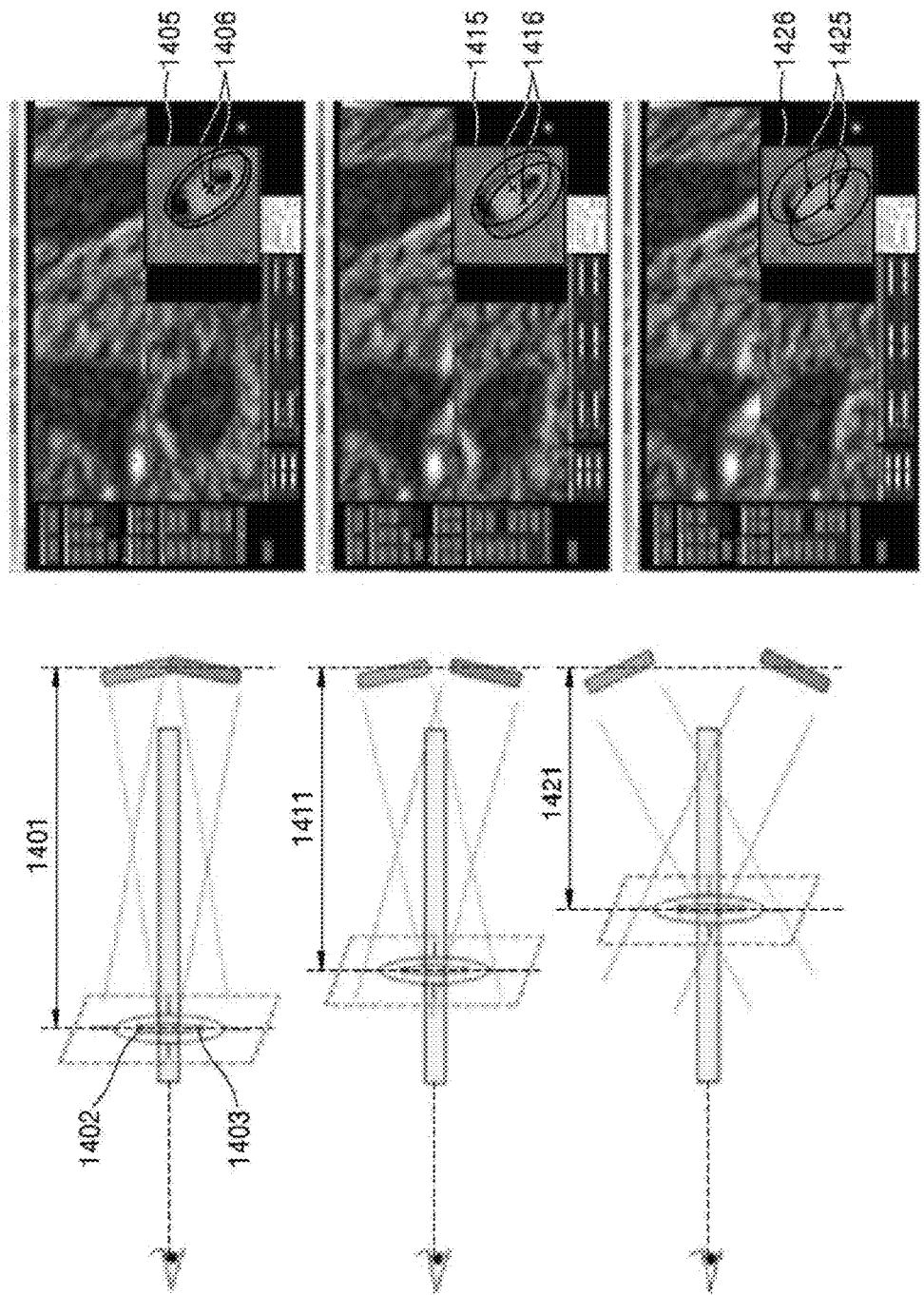
FIG. 14 is another exemplary view of an observation plane, a point, and a plurality of virtual rays, according to an embodiment of the present invention.

Referring to FIG. 14, when the 3D coordinates, which is 3D geometry information of the marker, is obtained, the processor 130 may generate the marker comprising an R marker 1402 and an L marker 1403, and allow the marker to have a predetermined depth value. In this case, the marker 1402 indicates a marker that is displayed on a right (R) image included in a stereo image; the L marker 1403 indicates a marker that is displayed on a left (L) image included in the stereo image.

The processor 130 sets a depth value to the marker, and thus display the marker on a stereo image. Referring to a stereo image 1405 of FIG. 14, a stereo marker 1406 is shown.

In specific, when a first depth 1401 is set to the marker, the stereo marker 1406 is displayed on the stereo image 1405, which is a 3D ultrasound image, such that the stereo marker 1406 corresponds to the first depth 1401. In specific, the stereo marker 1406 is located on a point corresponding to the 3D coordinate values of the marker obtained by the processor 130, but may have a different depth value according to intervals (for example, a focal distance) between the R marker 1402 and the L marker 1403. Also, when a second depth 1411 is set to the marker, a stereo marker 1416 is displayed on a stereo image 1415, which is a 3D ultrasound image, such that the stereo marker 1416 corresponds to the second depth 1411. In addition, when a third depth 1421 is set to the marker, a stereo marker 1426 is displayed on the stereo image 1425, which is a 3D ultrasound image, such that the stereo marker 1426 corresponds to the third depth 1421.

Also, perspective of the marker may be rendered by locating the 3D marker on a reference plane of the 3D ultrasound image (for example, a display panel plane of the display unit 150), and then adjusting a depth value of the object. For example, if the object is disposed far behind the reference value, the object may seem to be far away from the user. In this case, since the marker is on the reference plane, but the object is disposed far away from the reference plane, the marker may seem to be relatively closer to the user. As another example, if the object is in front of the reference value, the object may seem to be near the user. In this case, since the marker is on the reference plane, but the object is disposed near the reference plane, the marker may seem to be relatively further away from the user.

As illustrated in FIG. 14, when the marker is 3-dimensionally displayed by using the stereo method, it is possible to mark any point in the object. In detail, it is even possible to mark a predetermined point on an empty space in the object, which may not be displayed by using the ray-casting method.

Referring back to FIG. 1, the storage unit 140 stores the ultrasonic data that is obtained by the ultrasonic data obtaining unit 110, the input information received by the user input unit 120, the volume data VD generated by the processor 130, and the predetermined reference value.

The display unit 150 displays the 3D ultrasound image generated by the processor 130, a 2D section image generated by the processor 130, and the 3D marker.

As described above, according to the one or more of the above embodiments of the present invention, a 3D marker may be directly set on a 3D image without using a 2D image. In addition, not only is it possible to set the 3D marker on the 3D image, but it may also possible to provide a sectional image that corresponds to a random section of the 3D image, and a 2D marker may be set on a sectional image. Thus, 2D location information and 3D location information of a target object may be easily provided to a user.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A medical system comprising:
   an image data obtaining unit configured to obtain image data that corresponds to a 3-dimensional (3D) image of an object, the object comprising a target object;
   a user input unit configured to receive input information; and
   a processor configured to generate 3D data by using the image data, generating the 3D image by using the 3D data, detect 3D geometry information that corresponds to a 3D marker, including depth information, in the 3D data based on the input information, and set the 3D marker on the 3D image based on the 3D geometry information that is detected;
   wherein the input information comprises first input information for setting a location corresponding to the 3D marker and third input information for setting a reference value for detecting the 3D geometry information of the 3D marker in the 3D image in a depth direction, wherein the reference value is set for marking a boundary of the target object;
   wherein the processor is configured to set the reference value that corresponds to the target object, based on the third input information.

2. The medical system of claim 1, wherein the input information further comprises: second input information for selecting the target object.

3. The medical system of claim 2, wherein the processor is configured to set the reference value that corresponds to the target object based on the second input information.

4. The medical system of claim 1, wherein the first input information is information related to setting a point corresponding to the location,
   wherein the processer is configured to:
   set an observation plane that is formed of a plurality of pixels, based on the 3D data;
   detect a pixel which is on the observation plane corresponding to the point set by the first input information;
   project a virtual ray from the pixel that is detected to the 3D data;

obtain a sampling point and a sampling value of the sampling point by sampling the virtual ray at a predetermined sampling interval;

detect, according to the sampling value, a voxel that corresponds to the reference value from the 3D data; and determine 3D geometry information of the point by using 3D geometry information of the voxel that is detected.

5. The medical system of claim 4, wherein the processor is configured to:

cumulatively add a plurality of sampling values in a proceeding direction of the virtual ray; and determine that a voxel, which has a sum of cumulatively added sampling values that is the first to exceed or be equal to the reference value, is the voxel that corresponds to the reference value.

6. The medical system of claim 4, wherein the processor is configured to:

compare a plurality of sampling values and a predetermined threshold value, and then detect whether any of the plurality of sampling values is greater than or equal to the predetermined threshold value;

cumulatively add the plurality of sampling values that are detected in a proceeding direction of the virtual ray VR; and determine that a voxel, which has a sum of cumulatively added sampling values that is the first to exceed or be equal to the reference value, is the voxel that corresponds to the reference value.

7. The medical system of claim 4, wherein the processor is configured to:

compare a plurality of sampling values and the reference value, and thus detects a sampling value that is the first to exceed or be equal to the reference value, from among the plurality of sample values; and determine that a voxel that corresponds to the sampling value that is detected, is the voxel that corresponds to the reference value from the 3D data.

8. The medical system of claim 4, wherein the processor is configured to project at least two virtual rays that respectively correspond to different angles, from the pixel that is detected.

9. The medical system of claim 4, wherein the processor is configured to detect the 3D geometry information by using a perspective ray-casting method.

10. The medical system of claim 1, wherein the processor is configured to:

set first section in the 3D image;

generate a sectional image corresponding to the first section by using the 3D data; and set a 2D marker on the sectional image, based on the 3D geometry information that corresponds to the 3D marker.

11. A method of setting a 3D marker by a medical imaging apparatus, the method comprising:

a) obtaining, by an image data obtaining unit, image data that corresponds to a 3-dimensional (3D) image of an object, the object comprising a target object;

b) generating, by a processor, 3D data by using the image data;

c) generating, by a processor, the 3D image by using the 3D data;

d) receiving, by a user input unit, input information of the user;

e) detecting, by a processor, 3D geometry information that corresponds to the 3D marker and that reflects a predetermined depth in the 3D data based on the input information; and f) setting, by a processor, the 3D marker on the 3D image based on the 3D geometry information that is detected, wherein the input information comprises first input information for setting a location corresponding to the 3D marker, and third input information for setting a reference value for detecting the 3D geometry information of the 3D marker in the 3D image in a depth direction, wherein the reference value is set for marking a boundary of the target object, and wherein the e) detecting, by a processor, 3D geometry information comprises setting the reference value that corresponds to the target object, based on the third input information.

12. A medical imaging apparatus comprising:

a display unit configured to display a 3-dimensional (3D) ultrasound image generated by using 3D data;

a user input unit configured to receive first input information for selecting a predetermined location of the 3D ultrasound image and third input information for setting a reference value for detecting the 3D geometry information of the 3D marker in the 3D image in a depth direction, wherein the reference value is set for marking a boundary of the target object; and a processor configured to detect 3D geometry information of a 3D marker, including depth information, that corresponds to the predetermined location in the 3D data based on the first input information, set the 3D marker on the 3D image based on the 3D geometry information that is detected, wherein the processor is further configured to set the reference value according to portions of an object that is marked by the 3D marker and the third input information.

13. The medical imaging apparatus of claim 12, wherein the processor is configured to obtain depth information of the 3D ultrasound image, and renders perspective to the 3D marker by using the depth information.

14. The medical imaging apparatus of claim 12, wherein the display unit is configured to display the 3D marker on the 3D ultrasound image.

15. The medical imaging apparatus of claim 12, wherein the first input information is information related to setting a point corresponding to the location;

wherein the processor is configured to:

set an observation plane that is formed of a plurality of pixels, based on the 3D data;

detect a pixel on the observation plane which corresponds to the point set by the first input information;

project the virtual ray from the pixel that is detected to the 3D data;

obtain a sampling point and a sampling value of the sampling point by sampling the virtual ray at a predetermined sampling interval;

detect, according to the sampling value, a voxel that corresponds to the reference value from the 3D data; and determine 3D geometry information of the point by using 3D geometry information of the voxel that is detected.

16. The medical imaging apparatus of claim 12, wherein the processor is configured to show a predetermined depth of the 3D marker by using a stereo method.

* * * * *